United States Patent
Heyns et al.

(10) Patent No.: US 9,526,674 B2
(45) Date of Patent: Dec. 27, 2016

(54) MANEUVERABLE NASOENTERIC FEEDING TUBE

(75) Inventors: Armand Heyns, Topeka, KS (US);
Johannes Heyns, Topeka, KS (US);
Kyli S Beattie, San Jose, CA (US);
Dan Clinesmith, Overland Park, KS (US)

(73) Assignee: The University of Kansas, Lawrence, KS (US)

( * ) Notice: Subject to any disclaimer, the term of this patent is extended or adjusted under 35 U.S.C. 154(b) by 210 days.

(21) Appl. No.: 14/235,339

(22) PCT Filed: Jul. 27, 2012

(86) PCT No.: PCT/US2012/048495
§ 371 (c)(1),
(2), (4) Date: Feb. 19, 2014

(87) PCT Pub. No.: WO2013/016616
PCT Pub. Date: Jan. 31, 2013

(65) Prior Publication Data
US 2014/0163528 A1  Jun. 12, 2014

Related U.S. Application Data

(60) Provisional application No. 61/512,298, filed on Jul. 27, 2011.

(51) Int. Cl.
*A61J 15/00* (2006.01)
*A61M 25/00* (2006.01)
(Continued)

(52) U.S. Cl.
CPC ............ *A61J 15/0007* (2013.01); *A61B 90/39* (2016.02); *A61J 15/0069* (2013.01); *A61M 25/005* (2013.01); *A61M 25/0014* (2013.01); *A61M 25/0051* (2013.01); *A61M 25/0102* (2013.01); *A61M 25/0136* (2013.01); *A61M 25/0138* (2013.01); *A61M 25/0141* (2013.01);
(Continued)

(58) Field of Classification Search
CPC ................. A61M 25/0013; A61M 25/0051; A61M 25/0102; A61M 25/0138; A61M 25/0147
See application file for complete search history.

(56) References Cited

U.S. PATENT DOCUMENTS 2,498,692 A * 2/1950 Mains .................. A61M 25/10
604/915
4,547,192 A 10/1985 Brodsky et al.
(Continued)

FOREIGN PATENT DOCUMENTS

WO  2004/012804 A2  2/2004

*Primary Examiner* — Andrew Gilbert
(74) *Attorney, Agent, or Firm* — Maschoff Brennan, PLLC

(57) ABSTRACT

A maneuverable feeding tube system can include: a feeding tube having an internal lumen and distal opening; a maneuverable tube having a flexible distal end being located within the internal lumen of the feeding tube such that the flexible distal end is associated with the distal opening of the feeding tube, wherein the flexible distal end includes one or more flex members; a control member operably coupled to a flexible distal end of the maneuverable tube and extending through the internal lumen of the feeding tube; and a port coupled to a proximal end of the feeding tube with the control member extending therethrough.

21 Claims, 11 Drawing Sheets

(51) Int. Cl.
*A61M 39/08* (2006.01)
*A61M 25/01* (2006.01)

(52) U.S. Cl.
CPC ........ *A61M 25/0147* (2013.01); *A61M 39/08* (2013.01); *A61J 15/0088* (2015.05); *A61M 25/0097* (2013.01); *A61M 2039/085* (2013.01); *Y10T 29/49826* (2015.01)

(56) References Cited

U.S. PATENT DOCUMENTS

| | | | | |
|---|---|---|---|---|
| 4,661,110 A | * | 4/1987 | Fortier | A61M 39/20 604/256 |
| 4,769,014 A | * | 9/1988 | Russo | A61M 25/01 604/270 |
| 4,874,365 A | * | 10/1989 | Frederick | A61J 15/0061 604/270 |
| 4,898,577 A | * | 2/1990 | Badger | A61M 25/0152 604/528 |
| 4,911,148 A | * | 3/1990 | Sosnowski | A61B 1/0051 600/136 |
| 5,057,093 A | * | 10/1991 | Clegg | A61M 39/10 128/912 |
| 5,080,650 A | * | 1/1992 | Hirsch | A61J 15/0015 604/104 |
| 5,234,417 A | * | 8/1993 | Parks | A61J 15/0026 16/108 |
| 5,242,389 A | * | 9/1993 | Schrader | A61J 15/0007 600/585 |
| 5,290,250 A | * | 3/1994 | Bommarito | A61M 25/04 604/175 |
| 5,334,145 A | * | 8/1994 | Lundquist | A61M 25/0147 604/95.04 |
| 5,527,280 A | * | 6/1996 | Goelz | A61J 15/0015 604/103.1 |
| D373,418 S | * | 9/1996 | Szpak | D24/112 |
| 5,658,253 A | * | 8/1997 | Piontek | A61M 25/0102 604/170.02 |
| 5,871,467 A | * | 2/1999 | Reuning | A61J 15/0015 604/264 |
| 6,464,686 B1 | * | 10/2002 | O'Hara | A61B 17/3415 604/256 |
| 6,582,395 B1 | * | 6/2003 | Burkett | A61M 25/04 604/910 |
| 6,595,971 B1 | * | 7/2003 | von Dyck | A61F 5/442 604/334 |
| 7,628,775 B2 | * | 12/2009 | Adams | A61M 25/02 604/246 |
| 8,858,533 B2 | * | 10/2014 | Downing | A61M 39/12 604/537 |
| 2003/0009152 A1 | * | 1/2003 | O'Hara | A61B 17/3415 604/538 |
| 2004/0059257 A1 | * | 3/2004 | Gaber | A61M 25/0147 600/585 |
| 2005/0171468 A1 | * | 8/2005 | Wood | A61M 1/0058 604/39 |
| 2007/0088259 A1 | * | 4/2007 | Chu | A61J 15/0015 604/104 |
| 2009/0062772 A1 | * | 3/2009 | Wakeford | A61M 25/09041 604/516 |
| 2014/0330076 A1 | * | 11/2014 | Elia | A61B 1/015 600/104 |

* cited by examiner

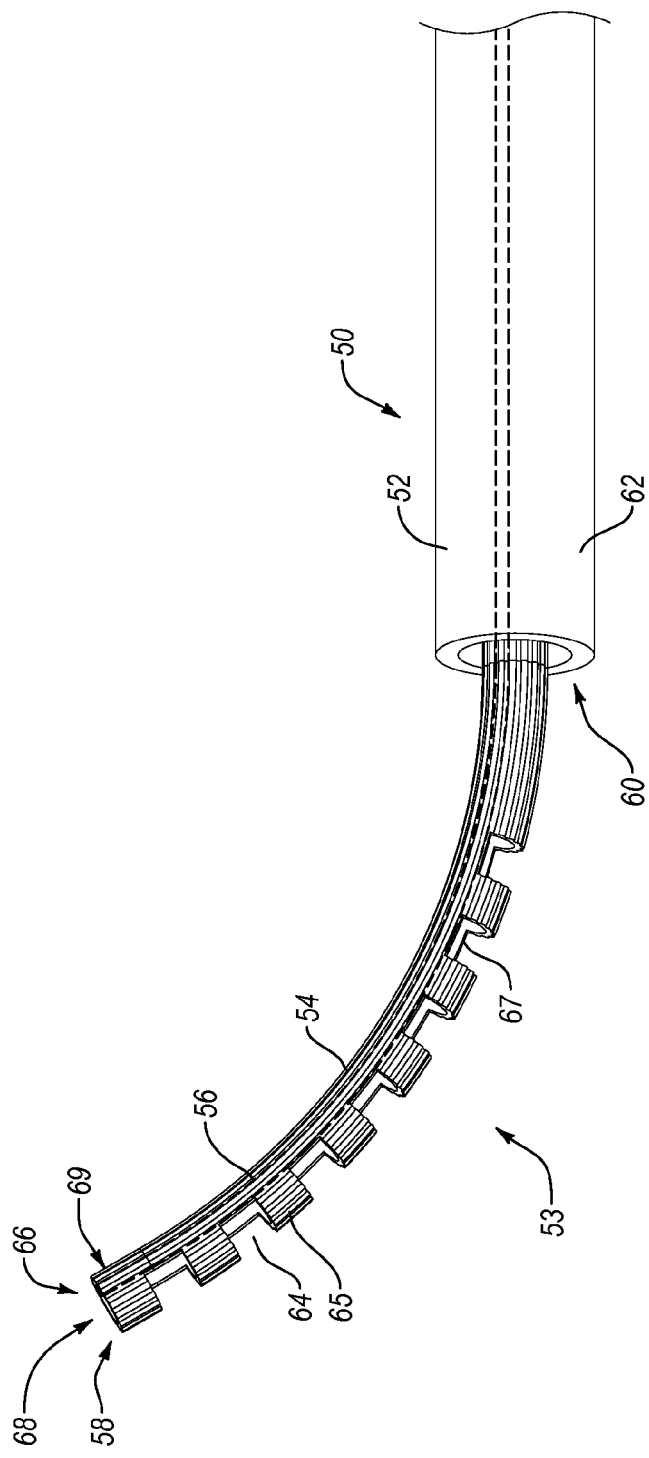
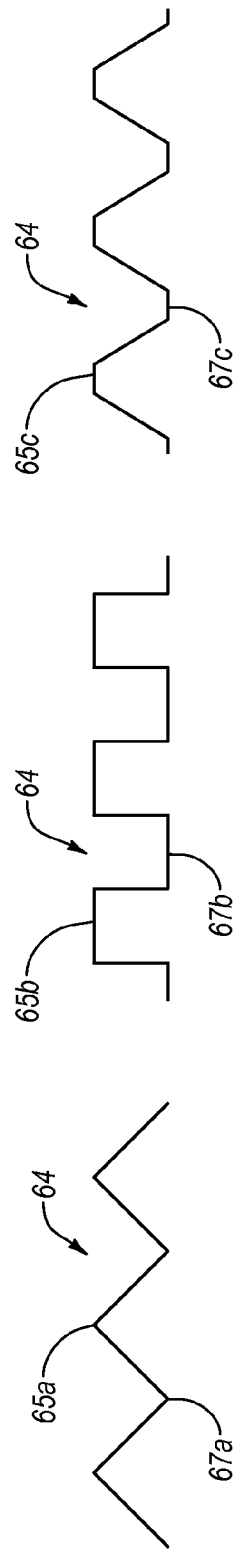
Fig. 5B
Fig. 5C

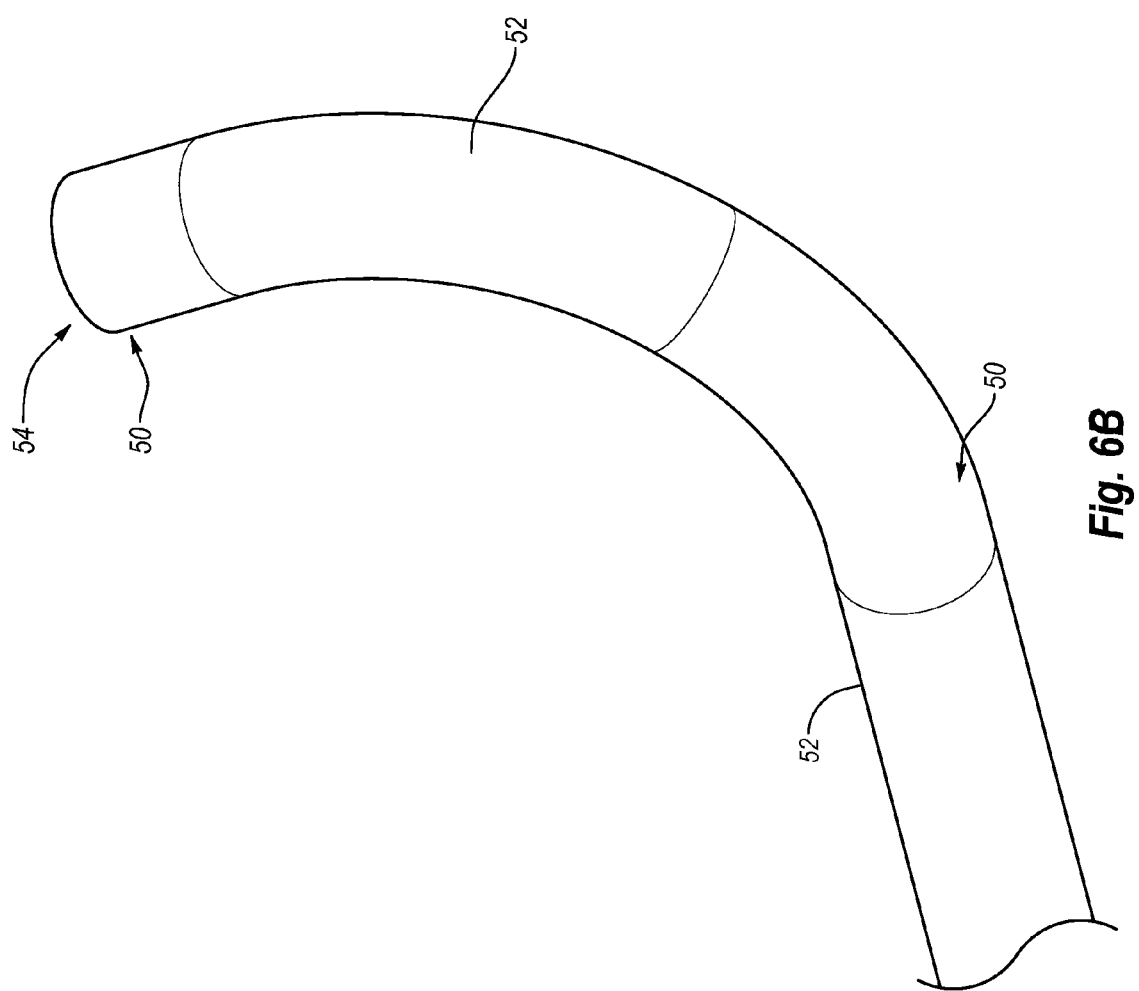

MANEUVERABLE NASOENTERIC FEEDING TUBE

CROSS-REFERENCE TO RELATED APPLICATION

This patent application claims the benefit of U.S. Provisional Application Ser. No. 61/512,298, filed on Jul. 27, 2011, which provisional application is incorporated herein by specific reference in its entirety.

BACKGROUND

Every year, approximately 14.9 million nasoenteric or nasogastric (NG) feeding tubes are used in hospitals in the United States. Current feeding tube technology can be difficult to place and time consuming to use. Often, the delivery and placement of the feeding tube is not initially successful, and different placement methods have to be pursued. The feeding tube can be difficult to insert and place within the desired location, with a reported success rate of just 60%. Feeding tubes also need to be replaced often, compounding the impact on physician and patient. Although use of a feeding tube is considered to be one of the safer ways of artificial feeding, there can be complications involved with the use of a feeding tube. The complications can include tube migration, fistula formation (e.g., the abnormal connection between two epithelium-lined passageways), skin abrasions, tube occlusion, vomiting, and metabolic effects. Many of these problems are from erroneous placement that injures the patient. Additionally, 3.2% of feeding tubes are misplaced in the patient's airway, which can result in such conditions as infection, blood poisoning, pneumonia, or death.

Therefore, there remains a need to have better feeding tubes that are configured for easier placement without complications or injuring the patient, and there remains a need to improve feeding tubes and the devices, systems, and methods used for the delivery and placement of the feeding tubes in the small intestine.

SUMMARY

In one embodiment, a maneuverable feeding tube system can include: a feeding tube having an internal lumen and distal opening; a maneuverable tube having a flexible distal end being located within the internal lumen of the feeding tube such that the flexible distal end is associated with the distal opening of the feeding tube, wherein the flexible distal end includes one or more flex members; a control member operably coupled to a flexible distal end of the maneuverable tube and extending through the internal lumen of the feeding tube; and a port coupled to a proximal end of the feeding tube with the control member extending therethrough.

In one embodiment, the system can include an actuator adapter having an actuator member. The actuator adaptor can be configured to be removably coupled to the port such that the control member extends through an internal conduit of the actuator adapter and is operably coupled with the actuator member.

In one embodiment, the system can include a luer lock adapter having a luer lock end. The luer lock adaptor can be configured to be removably coupled to the port such that the luer lock end is fluidly coupled with the feeding tube. The luer lock can be generically referred to as a ported adapter, which ported adapter can be configured herein and include a ported member that can couple to food reservoirs. As such, the ported member includes a port that can be removably coupled to a food reservoir, saline bag, or the like. As such, the ported member can function similar to a luer lock without being a luer lock.

In one embodiment, the system can include an adapter cap configured to be removably coupled to the port. The adapter cap can be configured to seal the port when coupled thereto.

In one embodiment, the actuator adapter, luer lock adapter, and adapter cap can be flexibly coupled together through elongate flexible members, such as elongate plastic members or thin strap members. Optionally, the actuator adapter, luer lock adapter, and adapter cap can be flexibly coupled to the port through elongate flexible members. Optionally, the actuator adapter, luer lock adapter, and adapter cap can be separate members.

In one embodiment, the feeding tube includes a biocompatible material that is flexibly resilient, such as a PVC or polyurethane polymer tube. In one aspect, the feeding tube can include a durometer of about 55 A or is more flexible or stiffer. However, it should be understood that the feeding tube can be prepared from any suitable material, such as known feeding tube materials, and can have a durometer within +/−5 or 10 of 55 A.

In one embodiment, the maneuverable tube includes a biocompatible material that is flexibly resilient. In one aspect, the maneuverable tube includes a polytetrafluoroethylene or polyurethane polymer tube. In one aspect, the maneuverable tube includes a durometer of about 55 A or 50 D or stiffer, and is stiffer than the feeding tube. However, it should be understood that the maneuverable tube can be prepared from any suitable material, such as known feeding tube materials or catheter materials, and can have a durometer within +/−5 or 10 of 55 A or 50 D. The feeding tube and maneuverable tube can be of the same material, where the maneuverable tube fits within the lumen of the feeding tube.

In one embodiment, the one or more flex members at least partially define flex gaps located between two adjacent flex members. In one aspect, the flexible distal end is configured to facilitate bending when a force is applied thereto, such as by flex gaps collapsing so that the flex members move toward each other. In one aspect, the flex gaps between the flex members are relief points for flexing and bending or pivoting. In one aspect, the flex members are separated by flex gaps that provide for increased flexibility of the distal portion compared to without the flex gaps. In one aspect, the flex gaps are configured as slits in the body of the maneuverable tube. In one aspect, the flex members are separated by flex gaps having troughs formed in the maneuverable tube. In one aspect, the flex members are separated by open spaces formed into the maneuverable tube. In one aspect, the flex members are accordion members. In one aspect, the flex members are separated by flex gaps that extend at least half way through the diameter of the maneuverable tube. In one aspect, the flex members are separated by flex recesses that do not extend to a lumen of the maneuverable tube, where the maneuverable tube can be a tube with a lumen or a solid cylinder member. In one aspect, the flex gaps are partial annular gaps or "C" shaped gaps in the maneuverable tube. In one aspect, the flex members are located on one side of the maneuverable tube.

In one embodiment, the system can include two or more control members. The control members can be coupled to the maneuverable tube at the flexible distal portion on opposite sides. En one aspect, the control member is monofilament or multifilament, a wire, a cord, or string or combination thereof. The control member can be located in a lumen of the maneuverable tube. The control member can be located between the maneuverable tube and feeding tube. In one aspect, the control member can be coupled to an actuator member of an actuator adaptor that is operably couplable to the port. In one aspect, the control member can be coupled to the maneuverable tube with a coupling member. In one aspect, the control member can be coupled to one or more of the flex members. In one aspect, the control member can be coupled to a distal end of the maneuverable tube. In one aspect, the control member can be coupled to the maneuverable tube on the same side as the flex members. In one aspect, a control member can be coupled to an opposite side of the maneuverable tube from the flex members. In one aspect, two or more control members are evenly distributed around the circumference of the maneuverable tube.

In one embodiment, one or more of the feeding tube, maneuverable tube, and control member include one or more radiopaque members or radiopaque indicia. In one aspect, the radiopaque members or indicia are located at a distal end of the feeding tube, maneuverable tube, and/or control member. In one aspect, the radiopaque members or indicia are embedded within the feeding tube and/or maneuverable tube. In one aspect, the control member is prepared from a radiopaque material.

In one embodiment, one or more of the feeding tube, maneuverable tube, or control member is devoid of a radiopaque material.

In one embodiment, a method of manufacturing the maneuverable feeding tube can include: obtaining the feeding tube having an internal lumen; obtaining a smaller tube having a cross-sectional profile that fits within the internal lumen of the feeding tube; forming flex members into the smaller tube at the distal portion thereof to form the maneuverable tube; coupling the control member to the flexible distal portion of the maneuverable tube; and combining the maneuverable tube with the feeding tube such that the maneuverable tube is located within the feeding tube such that their distal openings are associated. The method can also include obtaining the port, and coupling the port to a proximal end of the feeding tube. The method can also include preparing the monofilament or multifilament control member, and coupling the control member to the maneuverable tube.

In one embodiment, the manufacturing method can include: obtaining the actuator adaptor having the actuator member; coupling the actuator member to the control member; associating the actuator member with the actuator adaptor; and coupling the actuator adaptor to the port. In one aspect, the manufacturing method can include obtaining the luer lock adaptor, and coupling the luer lock adaptor to the port. In one aspect, the manufacturing method can include obtaining the adaptor cap, and coupling the adaptor cap to the port.

In one embodiment, a method of placing a feeding tube in a small intestine can include: providing the maneuverable feeding tube system; inserting a distal end of the maneuverable feeding tube system into a nostril of a subject; pushing the distal end of the maneuverable feeding tube system to the stomach with or without bending the flexible distal end of the maneuverable tube; pushing the flexible distal end of the maneuverable tube past the pylorus with or without bending the flexible distal end of the maneuverable tube; and locating the distal opening of the feeding tube within the small intestine. The method can include selectively bending the flexible distal end of the maneuverable tube by pulling the control member. The pulling on the control member can be performed by actuating the actuator member of the actuator adaptor that is coupled to the control member. In one aspect, the placement method can include disengaging the actuator adapter from the port. In one aspect, the placement method can include withdrawing the maneuverable tube from the feeding tube. In one embodiment, the placement method can include coupling the cap adapter to the port.

In one embodiment, a method of feeding a subject having the feeding tube delivered by the placement method can include coupling the luer lock adapter to the port, and coupling a medical device of food reservoir to the luer lock adapter. Food, such as liquid, gel, paste, or finely ground food can then be delivered via the feeding tube to the intestine of the subject.

In one embodiment, a method for replacing a used feeding tube with a new feeding tube can be performed. Such a replacement method can include: introducing a guide wire into the lumen of the feeding tube; and pushing the guide wire to the distal opening of the feeding tube. The replacement method can also include withdrawing the feeding tube over the guide wire. The replacement method can also include: placing a new feeding tube over the guide wire; and locating the distal opening of the new feeding tube to the distal end of the guide wire so as to be in the small intestine. However, the replacement can be performed without a guide wire, but can include using the maneuverable tube with or without being within the feeding tube. For example, the maneuverable tube can be placed, the actuator member decoupled from the maneuverable tube, and the feeding tube can be slid over the maneuverable tube.

In one embodiment, the placement of the feeding tube in the small intestine is conducted with saline being pushed through the lumen of the feeding tube.

In one embodiment, placement of the feeding tube in the small intestine is conducted with fluoroscopy. Alternatively, placement of the feeding tube in the small intestine is conducted without fluoroscopy.

DESCRIPTION OF FIGURES

FIGS. 5A-5B illustrate an embodiment of a feeding tube system having a feeding tube containing a maneuverable tube.

FIG. 5C illustrates embodiments of shapes of flexible distal ends of a maneuverable tube.

FIGS. 6A-6C illustrate embodiments of flexible portions of a maneuverable tube in straight and bent positions and extending from and located in a feeding tube.

DETAILED DESCRIPTION

Figure 1:
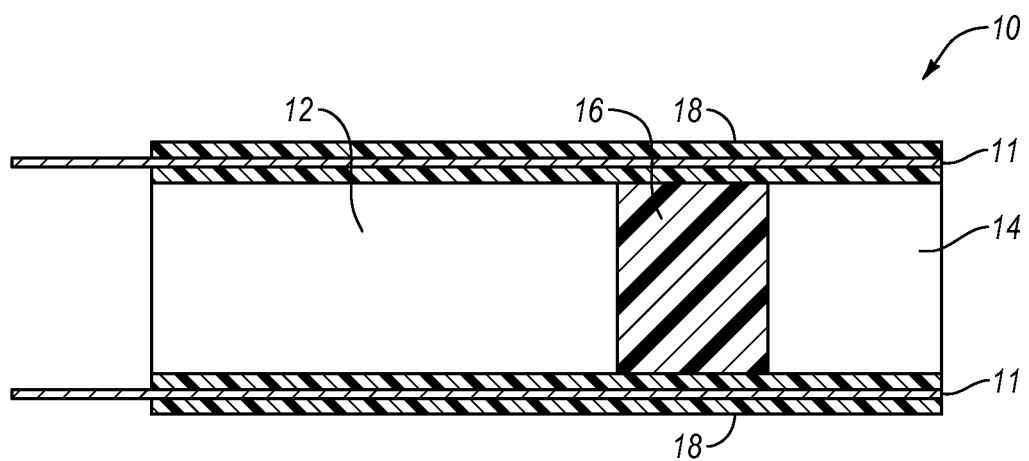
FIG. 1 illustrates an embodiment of a feeding tube having a flexible distal end.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to maneuverable feeding tubes and methods of use. The maneuverable feeding tubes can be nasoenteric feeding tubes or nasogastric (NG) feeding tubes. The maneuverable feeding tubes can be configured for single use, or configured for use as a guide during replacement of the previously placed feeding tube with a new feeding tube. The present invention also relates to maneuverable feeding tube systems that include a regular feeding tube containing a maneuverable tube. The maneuverable tube described herein can be used as feeding tube or used to deliver a feeding tube. The maneuverable tube can include a flexible distal end that can be selectively bent in one or more directions to allow for easier placement. The flexible distal end can be bent as needed during placement to allow for easier traversal of the distal end of the feeding tube from nose to intestine. The flexible distal end can be straightened and bent as desired by actuating a member operably coupled to the distal end.

In one embodiment, the inventive maneuverable tube can be sufficient as a guide for placement of a new feeding tube, and can be used as a guide for replacement of a subsequent feeding tube. Alternatively, once a feeding tube is placed with the maneuverable tube, a guide wire can be inserted through the feeding tube, and the guide wire left in place while the feeding tube is withdrawn and a new feeding tube delivered over the guide wire for placement. As such, the maneuverable tube can be used to prevent the requirement of performing the entire feeding placement procedure repeatedly with a new feeding tube. As such, the present invention can utilize technology for replacement of tubes in vascular procedures, commonly referred to as "Standard Seldinger Technique."

The maneuverable tube can be included in a feeding tube guide system configured for using a feeding tube as a guide. The feeding tube guide system can include a proximal end having a port that can be coupled to one or more different types of adaptors. The feeding tube guide system can include an actuator adaptor that has an actuator member that can selectively bend the flexible distal end of the feeding tube system when actuated. The feeding tube guide system can include a proximal end of the feeding tube, such as by having a luer lock or other rotatably coupling fastener member, being used to interface with current syringes for insertion of food or medicine. Also, the proximal end of the feeding tube system can be configured to have a removably couplable end member, such as a cap, that is configured to couple to the proximal end so as to seal the proximal end and inhibit any leaks that cause the medical personnel using a feeding tube to waste medication or food. Accordingly, the proximal end of the feeding tube system can be configured with a plurality of unique ports that are different to inhibit any confusion that may cause misconnections at the proximal end. That is, the unique ports can be configured for a specific use. For example, a food line can be separate from a drug line, and thereby the food port can be shaped different from a drug port. Also, the feeding tube port can have a unique port that is substantially different from other tubes used in a patient, such as being different from a common port to an IV.

In one embodiment, the feeding tube system can be configured for inserting the feeding tube into the patient, and guiding the tip of the feeding tube over gastric folds in the stomach and into the duodenum (e.g., the first section of the small intestine). The location of duodenal insertion into the stomach varies among patients, and thereby, the guidable tip of the feeding tube system can avoid problems previously associated with insertion of typical feeding tubes that are static or not selectively bendable because the typical tubes cannot be selectively bent and can become lodged in the opposite side of the stomach compared to the duodenum (the fundus). The guidable tip prevents the previously common method of trial and error placement, and reduces the possibility of injuring the patient. The guidable tip provides a feeding tube system that can be manipulated by the user (e.g., medical practitioner) in order to insert the tip of the feeding tube system into the duodenum quickly and safely while avoiding such issues as accidental entry into the trachea or having the tip get lodged in the fundus.

The present invention can include a feeding tube system that includes a nasogastric/nasoenteric feeding tube and a maneuverable tube. The nasogastric/nasoenteric feeding tubes are described herein. The nasogastric/nasoenteric feeding tubes are usually a small, cheap, and a less invasive form of feeding tube that is inserted through the nose into the either the stomach (nasogastric) or the small intestine (nasoenteric). However, the features of the present invention can be used in a nasogastric feeding tube systems as well as gastric feeding tube system.

In one embodiment, the guidable feeding tube systems and delivery methods can exclude fluoroscopy or include a substantially smaller amount of fluoroscopy. A common way of visualizing the insertion of the tube is through the use of fluoroscopy, which does cause some amount of radiation exposure. Now, the guidable tip allows placement without fluoroscopy. With the ability to maneuver the tip of the feeding tube, the angle of insertion can be changed, giving the physician, nurse, or other medical practitioner a better chance of inserting the guidable tip of the feeding tube into the small intestine in a shorter time span. This eases the process of insertion, and decreases the exposure to radiation due to the use of fluoroscopy. In some instance, fluoroscopy can be used to facilitate delivery of the maneuverable and/or feeding tubes or system thereof.

With the addition of the ability to maneuver the tip of the feeding tube, the chances for the medical practitioner to successfully insert the tube into the small intestine before giving up or causing damage to the patient are greatly increased. Once the guidable or maneuverable feeding tube system has been successfully inserted, the feeding tube can behave similarly to current feeding tubes, allowing for minimal training in the unique used with the guidable feeding tube design.

The guidable feeding tube system can include a feeding tube that has a maneuverable tip and a mechanism to control the tip's movement. The guidable feeding tube system can also include sealable ports, which may include luer lock ports, for leak prevention. Also, a non-locking port system can be included on an adapter that couples to the port of the feeding tube. The non-locking port system can include non-locking mechanisms, such as rotatable or snap-fit or friction fit, such as those known or developed. The guidable feeding tube system can also include a hole at the distal end (e.g., distal end is placed into the stomach or intestine) of the tube, which is configured for easy feeding tube replacement, such as in the case of clogging. The guidable feeding tube system can include the guidable tip that can be articulated in order to avoid the tip becoming lodged in a part of the stomach other than the pylorus (e.g., the pylorus is the section that attaches to the duodenum), where the guidable tip can be configured to have a large range of motion. It is thought that the ability to maneuver the tip during feeding tube placement can allow for a much shorter time to insert the tip into the duodenum.

Additionally, the easy replacement of the feeding tube, such as with the distal opening being placed at the end of the tube instead of on the side, can prevent repeated use of the insertion method, and can allow for a tube to be replaced without losing the location in the duodenum. The guidable feeding tube system and method can be configured similar to the Seldinger Technique and associated technologies. As such, the system can include a guide wire, which can be inserted through the placed feeding tube to the distal end, the feeding tube can be withdrawn over the guide wire, and a new feeding tube can be delivered and placed by being slid over the guide wire. In one aspect, the maneuverable tube having the flexible distal end can be used as the guide wire for replacement of the feeding tube. The maneuverable tube can be of any size sufficient for uses described herein.

With the maneuverable tip of the guidable feeding tube system, difficult areas, such as the trachea and fundus in the stomach (e.g., the upper portion of the stomach) are more easily passed, allowing the feeding tube to successfully reach the small intestine. By manipulating the tip of the feeding tube system, the tip of the feeding tube has a smaller chance of getting lodged in the fundus or other unfavorable location, which can avoid the tip going down the trachea into the lung where it could cause damage. The maneuverable tip configuration of the guidable feeding tube system can prevent the feeding tube from going down the trachea by allowing for enhanced manipulation of the tip and placement into the proper location by a medical practitioner.

In one embodiment, the guidable feeding tube system is configured as a single use device or single use system having feeding tube and maneuverable tube. The materials of the guidable feeding tube system are common in disposable medical equipment, which can include common plastics, rubbers, metals, or the like.

In one embodiment, the maneuverable tube is configured as a guidable feeding tube guide, which is adapted to receive the feeding tube thereover. The guidable feeding tube guide can be guided to the desired location, the general feeding tube can be placed over and guided over the guidable feeding tube, and the guidable feeding tube guide can be withdrawn through the feeding tube. If the guidable feeding tube guide having the maneuverable tube and maneuvering mechanism is removable from the general feeding tube, then the general feeding tube does not not have the maneuvering function, and is a normal feeding tube without a maneuvering mechanism. As such, a guidable feeding tube system or kit can include the guidable feeding tube guide as described herein along with a general feeding tube that includes an internal lumen that is dimensioned and configured to be received and slid over the outer surface of the guidable feeding tube guide. Alternatively, the guidable feeding tube guide can be provided alone for use with other or standard feeding tubes. Still alternatively, the guidable feeding tube guide can be used as the actual feeding tube, and may be dimensioned as the feeding tube as described herein.

In one embodiment, a system or kit having the guidable feeding tube guide can also include a guide wire. The guide wire can be used for replacement of a used feeding tube with a new feeding tube. The guide wire can be inserted through the used feeding tube, the used feeding tube is removed over the guide wire, and the new feeding tube is placed over and slid along the guide wire for placement. As such, the guide wire can function in order to guide a new feeding tube. In one option, the guidable feeding tube guide can be place, and then the guide wire inserted therethrough, the guidable feeding tube guide withdrawn over the guide wire, and the new feeding tube placed on and slid over the guide wire for placement.

FIG. 1 illustrates an embodiment of a guidable feeding tube 10. The feeding tube 10 includes a main tube 12 with a lumen, which can be configured as a common feeding tube. An end tube 14 with a lumen is located at the distal end. A flexible section 16 with a lumen is coupled between the main tube 12 and the end tube 14. The coupling can be by any manner, such as by being just adjacent, adhered, fastened, threaded, snap-fit, friction fit, or the like. The flexible section 16 can have any configuration that is highly flexible, accordion, ribbed, and may even be a gap. The flexible section 16 can include the notch features described in more detail herein. Also, the flexible section 16 can be a tube with substantially less rigidity than the main tube 12 and/or end tube 14. In any event, the flexible section 16 can allow for the end tube 14 to bend with respect to the main tube 12 as described herein. In order to facilitate bending, the guidable feeding tube 10 can include one or more control wires 11, which is shown to include two control wires 11.

The control wires 11 are shown to be included in control wire Conduits 18; however, the control wires 11 can be located internally within the internal lumens of the main tube 12, flexible section 16, and end tube 14. The control wires 11 are shown to be coupled to an end of the control wire conduits 18; however, the control wires 11 can be coupled to any portion of the control wire conduit 18 that corresponds with the end tube 14 or directly to any portion of the end tube 14. Pulling on one control wire 11 bends the guidable feeding tube 10 in that direction. Pulling on the other control wire 11 bends the guidable feeding tube in the other direction. When the guidable feeding tube 10 is bent, pushing on the appropriate control wire 11 straightens the guidable feeding tube. Such maneuverability allows for the end tube 14 to be bent and maneuvered with respect to the main tube 12. The angles of bending are described herein, and may be up to 90 degrees. Also, the end tube 14 may be substituted with another end member other than a tube, which other end member can be a cap, ball, rounded end, or the like that is attached to the one or more control wires 11 and capable of bending with respect to the main tube 12. Such guide wire and/or conduit configurations can be applied to any of the maneuverable tubes, maneuverable feeding tubes, and/or maneuverable feeding tube guides described herein.

Figure 2:
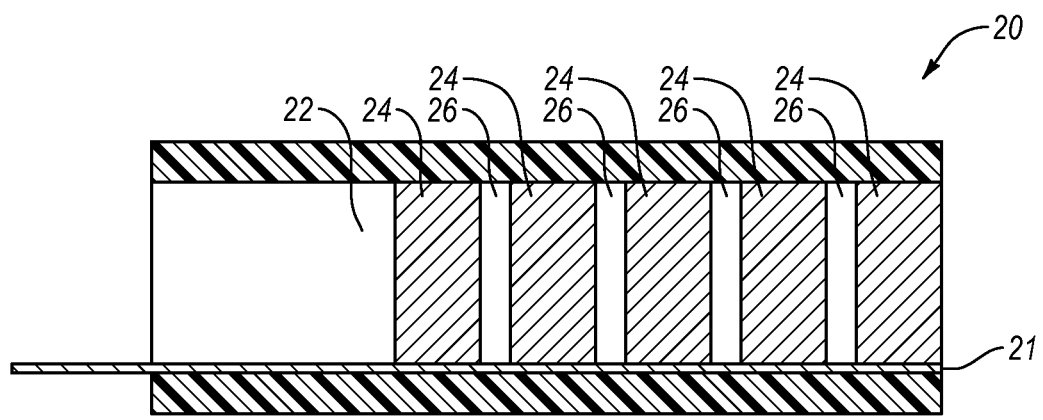
FIG. 2 illustrates an embodiment of a feeding tube having a flexible distal end.

FIG. 2 illustrates an embodiment of a guidable feeding tube 20. The feeding tube 20 includes a main tube 22, which can include rigid members 24 located within the internal lumen of the main tube 22. The rigid members 24 can be spaced apart from each other with annular gaps 26. Alternatively, the gaps 26 can be less rigid members. The rigid members 24 may be annular in shape with an internal lumen. A control wire 21 can be located in the internal lumen of the main tube 22, and attached to the end rigid member 24; however, it is possible that the wire is located in conduits. Also, the control wire 21 can be in an internal lumen of the annular rigid members 24, or between the rigid members and the main tube 22. The rigid members 14 can be substituted with other members, such as tubes, "C" shaped members, cones, or the like, which are located with gaps 26, which gaps 26 allow for the rigid members 24 and thereby the main tube 20 to bend. While one control wire 21 is shown, two, four, or more can be used. Usually, when two control wires are used, they are on opposite sides. When four control wires are used, they are usually at quadrant positions.

Figure 3:
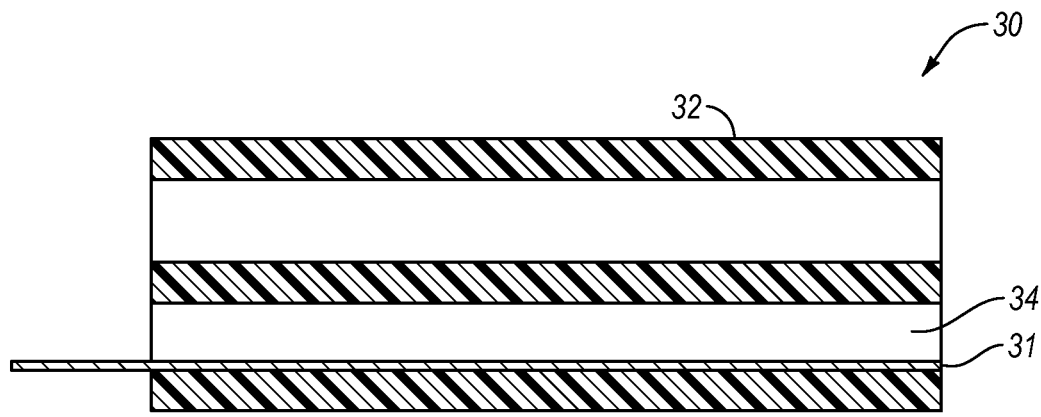
FIG. 3 illustrates an embodiment of a feeding tube having a flexible distal end.

FIG. 3 illustrates an embodiment of a guidable feeding tube 30. The feeding tube 30 includes a main feeding tube 32 coupled to a control wire conduit tube 34 having the control wire 31. While the main feeding tube 32 and control wire conduit tube 34 are shown to be the same size, the control wire conduit tube 34 having the control wire 31 can be smaller. While the control wire 31 is shown to be attached to the control wire conduit tube 34 away from the main feeding tube 32, the control wire can be coupled adjacent to the main feeding tube 32 or any position therebetween. Additionally, two, four, or more control wire conduit tubes 34 having control wires 31 can be coupled to a main feeding tube 32, such as at opposite or quadrant coupling positions.

Figure 4:
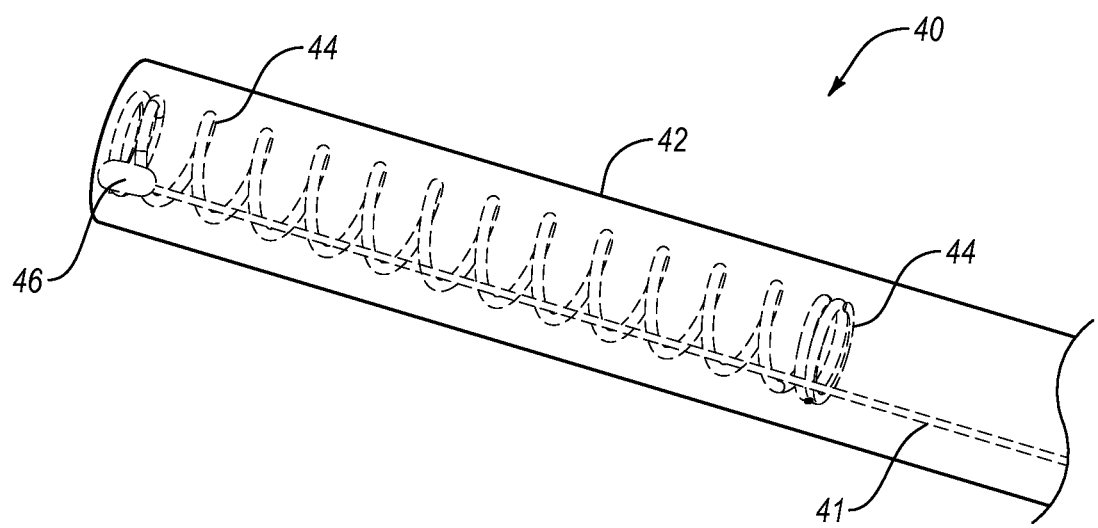
FIG. 4 illustrates an embodiment of a feeding tube having a flexible distal end.

FIG. 4 illustrates an embodiment of a guidable feeding tube 40. The feeding tube 40 includes a main feeding tube 42 having a spring 44 positioned at the distal end. The spring 44 includes the control wire 41 coupled to its distal end. A coupling member 46 can be used to couple the control wire to the spring 44, where the spring 44 may be a wound wire spring 44 as shown or any other type of spring. The coupling member 44 can be a weld, solder, fastener, adhesive, or the like. Also, two, four, or more control wires 41 can be coupled to opposite or quadrant positions on the distal end of the spring 42. While shown to be coupled at the very distal end of the spring 44, the control wire 41 may be at any reasonable position along the spring 44 that allows the spring 44 to bend upon tension to the control wire 41.

While the feeding tubes of FIG. 1-4 can be used as actual feeding tubes, the feeding tubes illustrated therein may also be used as guidable feeding tube guides or maneuverable tubes as described herein. The guidable feeding tube guides or maneuverable tubes can be used as guides for guidable placement of feeding tubes. The guidable feeding tube guides or maneuverable tubes can be located within an internal lumen of a feeding tube, and properly dimensioned so that the feeding tube can be slid over the guidable feeding tube guide or maneuverable tube, and such that the guidable feeding tube guide or maneuverable tube can be slid from the internal lumen of the feeding tube. Additionally, any of the guidable feeding tube guides or maneuverable tubes illustrated and described herein can be used as actual feeding tubes. Also, any of the features of any of the figures can be combined with any of the other figures and features provided herein.

Figure 5A:
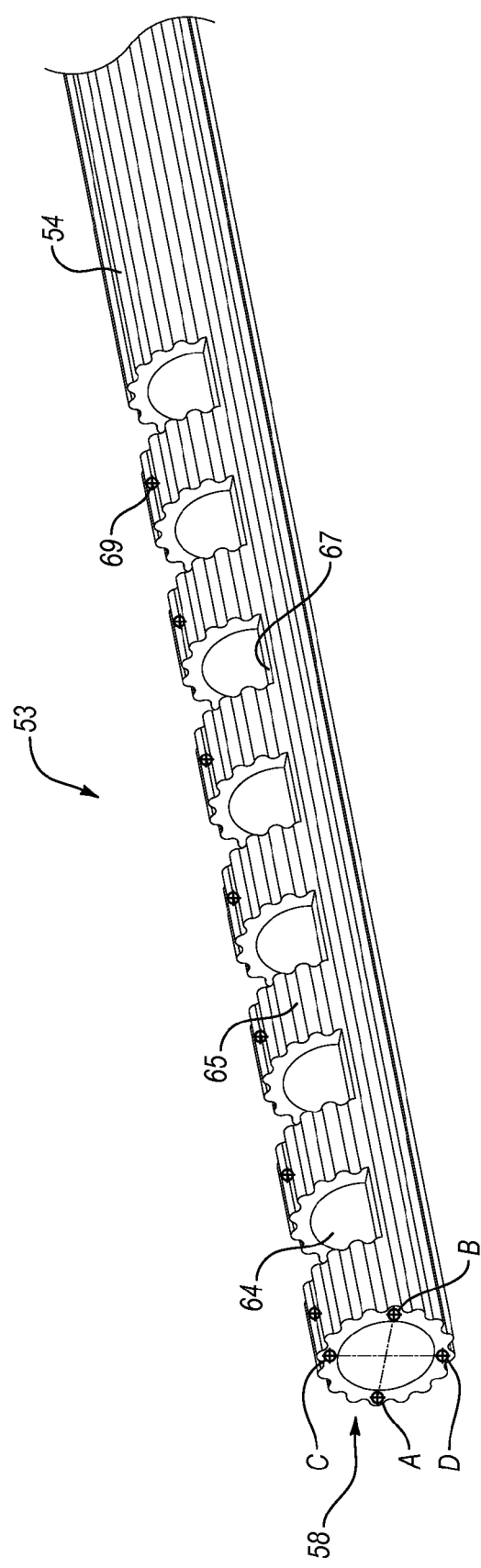

FIGS. 5A-5B illustrates an embodiment of a guidable feeding tube system 50. The guidable feeding tube system 50 generally includes a feeding tube 52 and a maneuverable tube 54 (e.g., guidable feeding tube guide). The feeding tube 52 includes a lumen 62 that contains the maneuverable tube 54. The maneuverable tube 54 includes a control member 56, which can be a pullable and/or pushable control wire. The control member 56 may also be configured as a strip or tube or elongate cylinder or other elongate member capable of functioning as described herein. The control member 56 can be coupled to the distal end portion 58 of the maneuverable tube 54. FIG. 5B illustrates the maneuverable tube 54 extending from a distal opening 60 of the feeding tube 52; however, in application the distal end 58 of the maneuverable tube 54 can extend from, can be at or aligned with, or can be in the distal opening 60 of the feeding tube 52. As such, the distal end 58 of the maneuverable tube 54 can be contained in or projecting through the distal opening 60. It should be understood that some protrusion of the distal end 58 of the maneuverable tube 54 may be allowable as long as the function and delivery is acceptable.

As shown, the maneuverable tube 54 can include a flexible portion 53 that provides the flexibility. The flexible portion 53 has protruding teeth members 65 separated by gaps 64 that extend partially through the body of the maneuverable tube 54. The protruding teeth members 65 have troughs 67 at the gaps 64. The protruding teeth member 65, gaps 64, and troughs 67 can have substantially any shape and dimension that allows for the flexible functionality as described herein. For example, thinner protruding teeth, deeper gaps, and/or wider troughs and number of the same can provide more flexible potential, which can cooperatively be adjusted in order to provide bending from 10 to 180 degrees (see FIG. 6B, which shows the end of the flexible portion 53 pointing nearly 180 degrees). Examples of maximum bending angle for the flexible portion 53 can include about 180, 170, 160, 150, 140, 130, 120, 110, 100, 90, 80, 70, 60, 50, 40, 30, 20, or 10 degrees, or any angle or angle range therebetween. However, bendability up to 90 degrees can be easily obtained.

FIG. 5C illustrates embodiments of shapes of the flexible portion of the maneuverable tube 54, which illustrates a saw tooth shape having sharp teeth 65*a* separated by gaps 64 that have sharp troughs 67*a* therebetween, blunt teeth 65*b* with blunt troughs 67*b*, and plateaued teeth 65*c* with flat troughs 67*c*.

The flexible portion 53 is coupled with the control member 56 at a coupling point 69. The coupling point 69 can be at any of the protruding teeth members 65, however, the most distal or end protruding tooth member 65 can be most preferred. The control member 56 is preferably coupled to a distal end or inside wall of the internal lumen of the flexible portion. That is, at an inside wall of a protruding tooth member 65.

The protruding teeth members 65 provide flexibility, and thereby act as bumpers to soften impact when pushed against tissue so as to reduce the potential for damage. For example, the protruding teeth members 65 distal from the coupling point 69 with the control member 56 can function as bumpers.

Figure 6A:
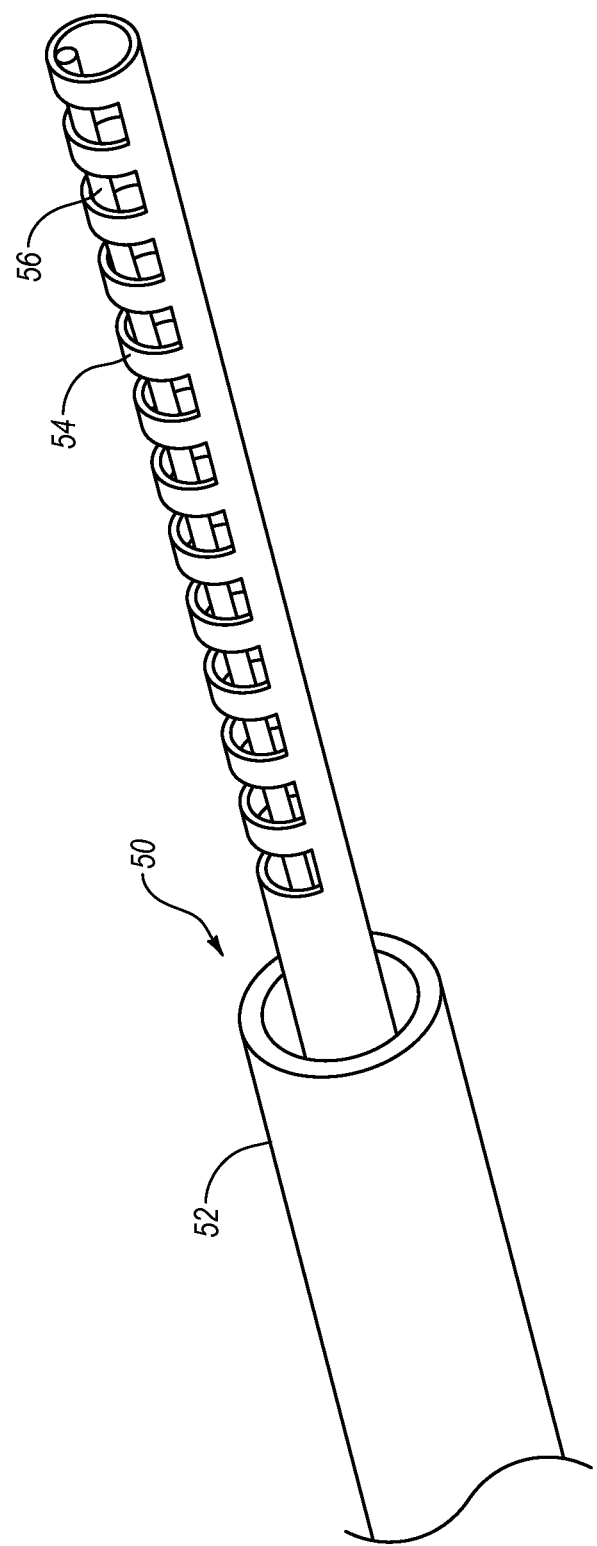
Figure 6B:
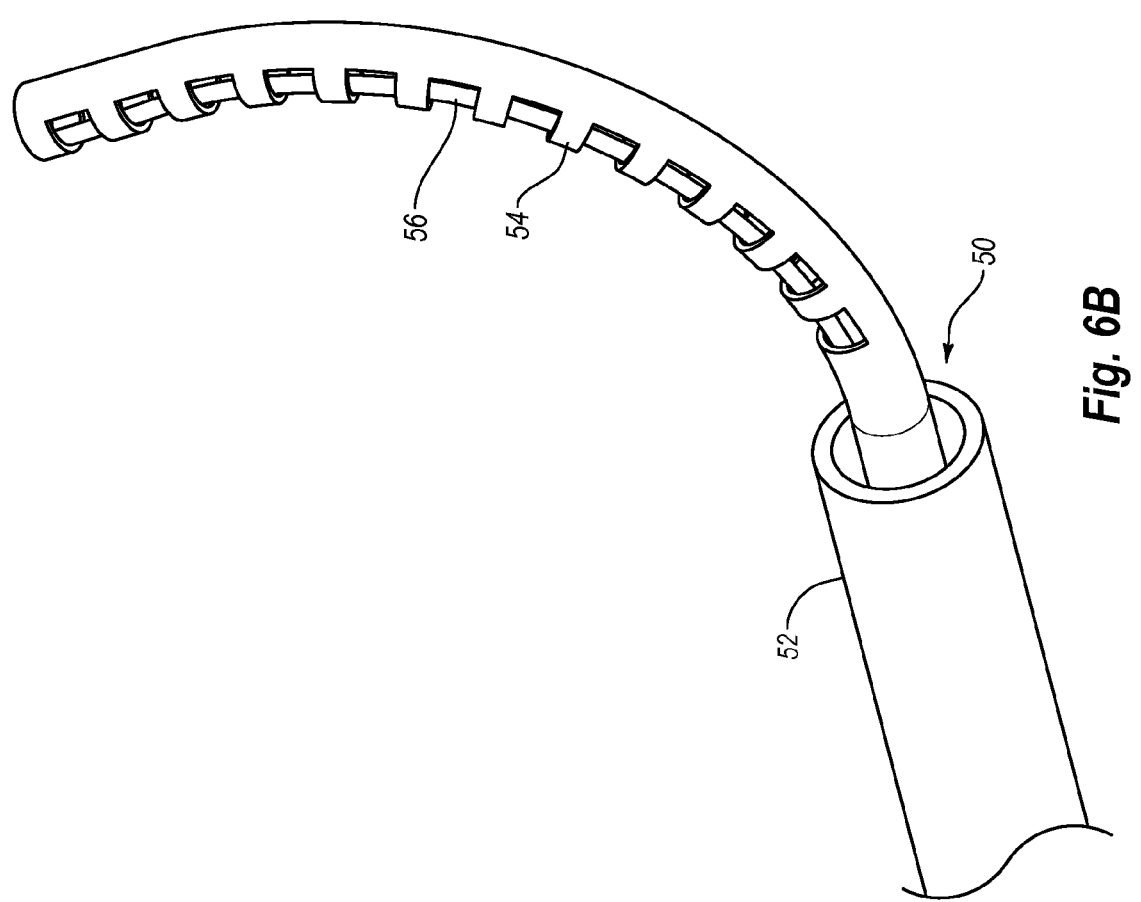

FIGS. 6A-6C shows the guidable feeding tube system 50, where FIG. 6A shows the guidable feeding tube system 50 with the maneuverable tube 54 being straight and protruding from the feeding tube 52, FIG. 6B shows the guidable feeding tube system 50 with the maneuverable tube 54 being bent and protruding from the feeding tube 52, and FIG. 6C shows the guidable feeding tube system 50 with the maneuverable tube 54 being bent and the feeding tube completely containing the maneuverable tube 54 therein. As such, the guidable feeding tube system 50 can be bent to a high angle while the maneuverable tube 54 is in or protruding from the feeding tube 52 and the feeding tube 52 can bend along with the bending of the maneuverable tube 54.

The feeding tube 52 and/or maneuverable tube 54 can be any type of standard feeding tube, which can be prepared from standard materials. The materials of the feeding tube 52 and/or maneuverable tube 54 can be modified so that the feeding tube system 50 has sufficient bendability and softness so as to be capable of being placed in the small intestine as described without damaging any anatomy of the subject receiving the feeding tube 54. The feeding tube 52 and/or maneuverable tube 54 can, for example, have the properties described herein and in connection with Table 1. The lengths of the feeding tube 52 and maneuverable tube 54 can vary, where the maneuverable tube can be shorter, same length, or longer than the feeding tube.

One feature of the feeding tube 52 is the internal lumen 62 that provides a conduit for the maneuverable tube 54, and allows for foods and nutrients to be provided directly to the subject when passed out of the distal opening 60. Similarly, the maneuverable tube 54 can have an internal lumen 66 having a distal opening 68. However, the maneuverable tube 54 can be a cylinder to flat strip without an internal lumen. When containing the internal lumen 66, the maneuverable tube 54 can function as a feeding tube, and can also be used to deliver liquids, such as food liquids or medications.

The maneuverable tube 54 can have properties similar to the feeding tube 52 with respect to materials for bendability and softness. The material for the maneuverable tube 54 can be selected to have bendability but also to have axial stiffness. It may be important for the maneuverable tube 54 to not deform axially so that the maneuverable tube 54 does not have an accordion-like deformation. The dimensions of the length of maneuverable tube can be substantially similar to common feeding tubes or as described herein. The cross-sectional profile can be dimensioned so as to be capable of fitting within the lumen 62 of the feeding tube 52. The maneuverable tube 54 can also include an internal lumen 66, which can extend from a distal opening 68 to a proximal end (not shown).

The distal end 58 of the maneuverable tube 54 can include flex gaps 64 separating flex member 65, which are illustrated to be slits cut into the body of the maneuverable tube 54. The flex gaps 64 allow for the distal end 58 to flex and bend so as to provide the maneuverability. The slit embodiment of the flex gaps 64 provide a gap of any dimension, which can expand to bend in one direction and collapse to bend in the other direction. While the flex gaps 64 are only shown on one side of the flexible portion 53, they can be on both sides, alternating from both sides, on quadrant sides, alternating on quadrant sides, or in any number in any position, and at any depth or dimension at the flexible portion 53. The maneuverable tube 54 is illustrated to include 7 slits that function as flex gaps 64; however, any suitable number of flex gaps 64 or flex members 65 can be included, such as from 1-20, 2-10, 3-9, 4-8, 5-7, or about 6, or more depending on the design. The flex gaps 64 and flex members 65 may also be configured as relief points that allow for bending of the maneuverable tube 54.

The flex gaps 64 can be slits having a rectangular shape, however, any suitable shape can be used, such as shapes similar to a V shape, C shape, U shape, W shape, or the like. The flex gaps 64 and/or flex members 65 can have a uniform dimension, or can taper. The flex members 64 can be mere slits without significant dimension when the maneuverable tube 54 is at rest and then open when bent, and the flex members 64 may be more trough-shaped so that there is a gap when at rest. Also, while the flex gaps 64 are illustrated to be cut through the body of the maneuverable tube 54 so as to define the shape of the flex member 65, the flex gaps 64 can be recessed portions or surface divots that do not cut into the lumen 66 of the maneuverable tube 54. The flex gaps 64 can be cut into the internal lumen 66 so as to expose holes through the maneuverable tube 54 to the internal lumen 66. When used as a feeding tube, the holes exposed to the internal lumen 66 by the flex gaps 64 can deliver feeding tube liquids or the like that commonly are provided by feeding tubes 52.

The distal end 58 of the maneuverable tube 54 can include the control member 56 attached thereto, which is illustrated to be a cord, but can also be a wire, string, or the like. The placement of the control member 56 can vary as long as it is able to impart bending to the distal end 58 of the flexible portion 53 to allow for maneuverability to the maneuverable tube 54. The control member 56 may be coupled to the body of the maneuverable tube 54 at any location along the distal end 58. However, the embodiment of the FIG. 5A shows the control member 56 to be coupled to the body between the most distal flex member 64 and distal opening 68 at a coupling point 69, and also shows other examples on where the control member 56 may be coupled identified by the four-point stars as the coupling points 69. In fact, the control member 56 can be located anywhere around the perimeter of the maneuverable tube 54; however locations on the quadrants relative to or on the flex members 65 may be preferred. Also, more than one control members 56 can be used, such as two or four control members 56. For example, two control members 56 can be located as identified with A and B or on C and D on FIG. 5A such that pulling on D expands the flex gaps 64 and pulling on C compresses the flex gaps 64. For example, two control members 56 can be located as identified with C and D on FIG. 5A such that pushing on D compresses the flex gaps 64 and pushing on C expands the flex gaps 64. It was found that only one control member 64 coupled to C was suitable and efficient. Coupling to A and/or B can also provide for control over bending.

Figure 7:
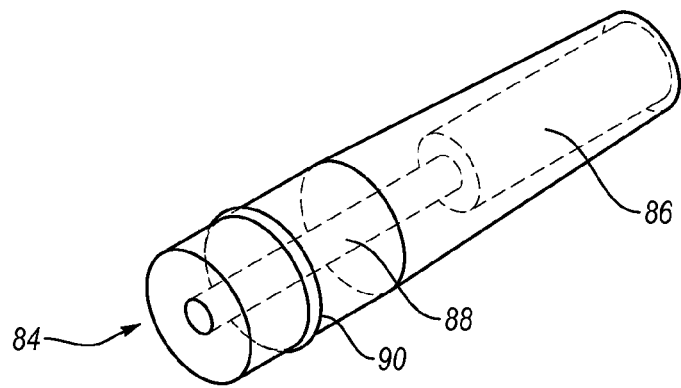
FIG. 7 illustrates an embodiment of a port that couples with adapters for a proximal end of a feeding tube.
Figure 10:
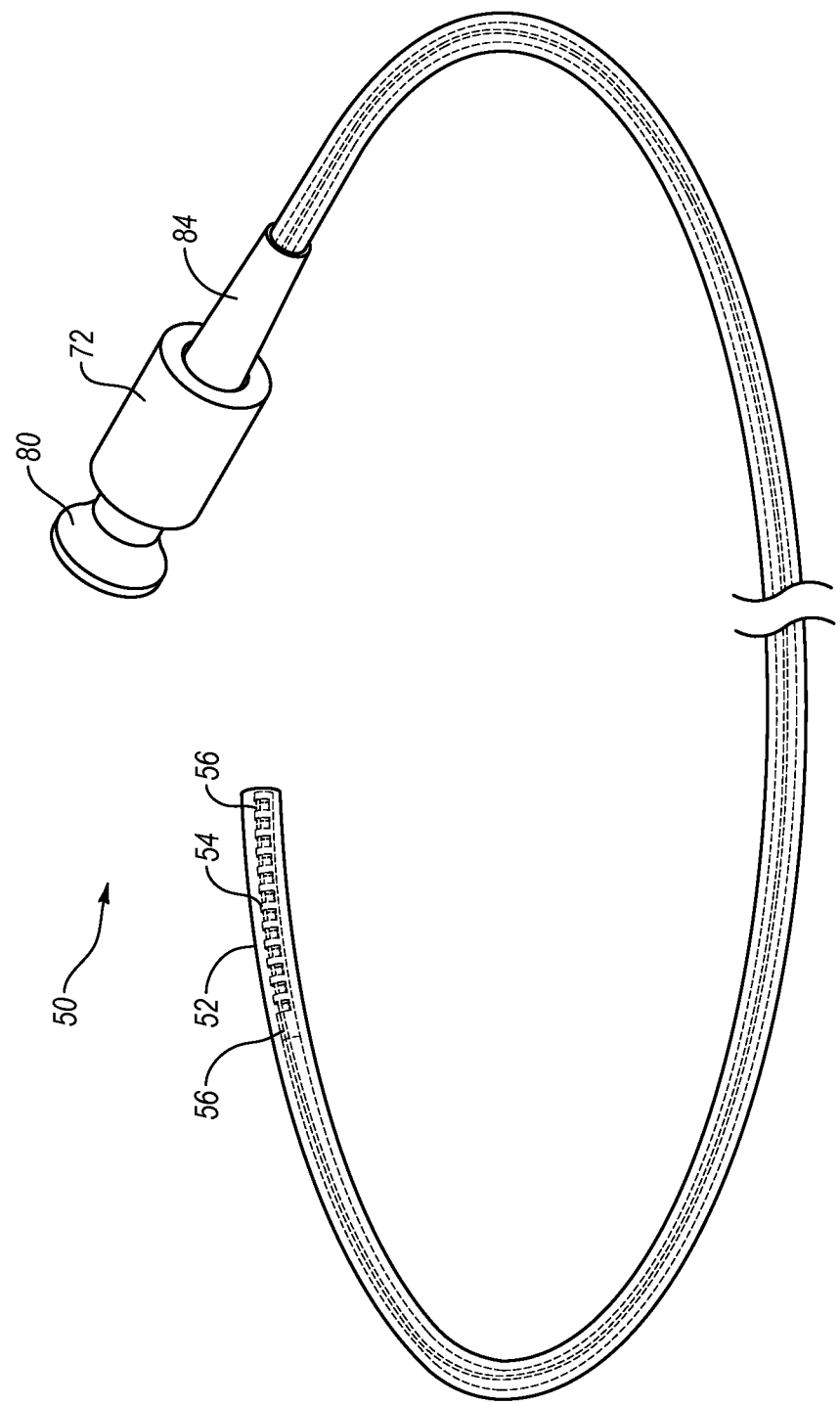
FIG. 10 illustrates a maneuverable feeding tube system having an actuator adaptor coupled to a port.

FIG. 7 shows an embodiment of a port 84 at the proximal end of the feeding tube system 50 (see FIG. 10 for entire feeding tube system). While the port 84 is illustrated to be cylindrical or conical, it can be any functional shape and can be configured as common ports of feeding tubes, such as luer locks or as shown in incorporated provisional application. The port 84 includes a recess 86 adapted to receive the proximal end of the feeding tube 52 or maneuverable tube 54 or both the feeding tube and maneuverable tube 54. The recess 86 is fluidly coupled with an internal conduit 88 of the port 84 that extends all the way through the port 84.

The port 84 can include a fastener member 90 that is configured to fasten to an adapter 72 that is described herein. As such, the port 84 and adapter 72 can include mating fastener members. The fastener member 90 shown is configured as a snap member such that the port 84 is received into and snaps within the adapter 72. Other fastener members can be threads, friction fittings, male-female attachments, or any other fastening members that can couple together the port 84 with the adapter 72.

Figure 8:
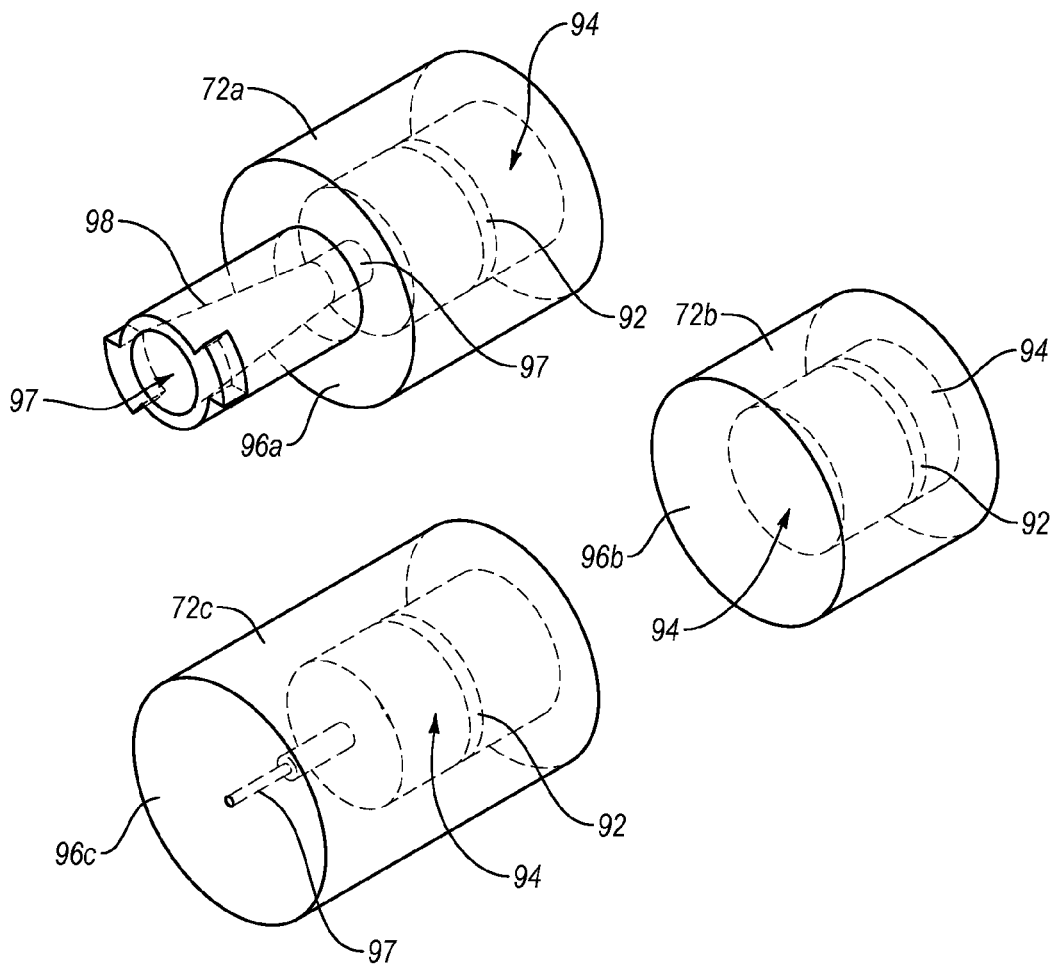
FIGS. 8-9 illustrate embodiments of adapters for a proximal end of a feeding tube that coupled with the port of the feeding tube.

FIG. 8 illustrates embodiments of three adapter designs, 72a, 72b, 72c that can be coupled with the port 84. Going clockwise from top left the adaptors can include: luer lock adapter 72a, inactivity adapter cap 72b, and actuator adapter 72c.

As shown, the luer lock adapter 72a includes a cavity 94 that receives the port 84 therein. The cavity 94 includes a fastener member 92 that mates with and fastens to the fastener member 90 of the port 84. The cavity 94 is fluidly coupled with an internal lumen 97 of a luer lock member 98. The luer lock member 98 extends from a distal end 96a.

As shown, the inactivity adapter cap 72b includes a cavity 94 that receives the port 84 therein. The cavity 94 includes a fastener member 92 that mates with and fastens to the fastener member 90 of the port 84. The distal end 96b is solid so that the adapter cap 72b seals the port 84. As such, the adapter cap 72b can be mounted to the port 84 to prevent fluids from entering or leaving the feeding tube or maneuverable tube.

As shown, the actuator adapter 72c includes a cavity 94 that receives the port 84 therein. The cavity 94 includes a fastener member 92 that mates with and fastens to the fastener member 90 of the port 84. The cavity 94 is fluidly coupled with a lumen 97 that extends to and out from the distal end 96c. The control wire or control member described herein can extend through the lumen 97 and therefrom. As such, the control wire or control member can be actuated through the lumen 97 of the actuator mechanism adapter.

Figure 9:
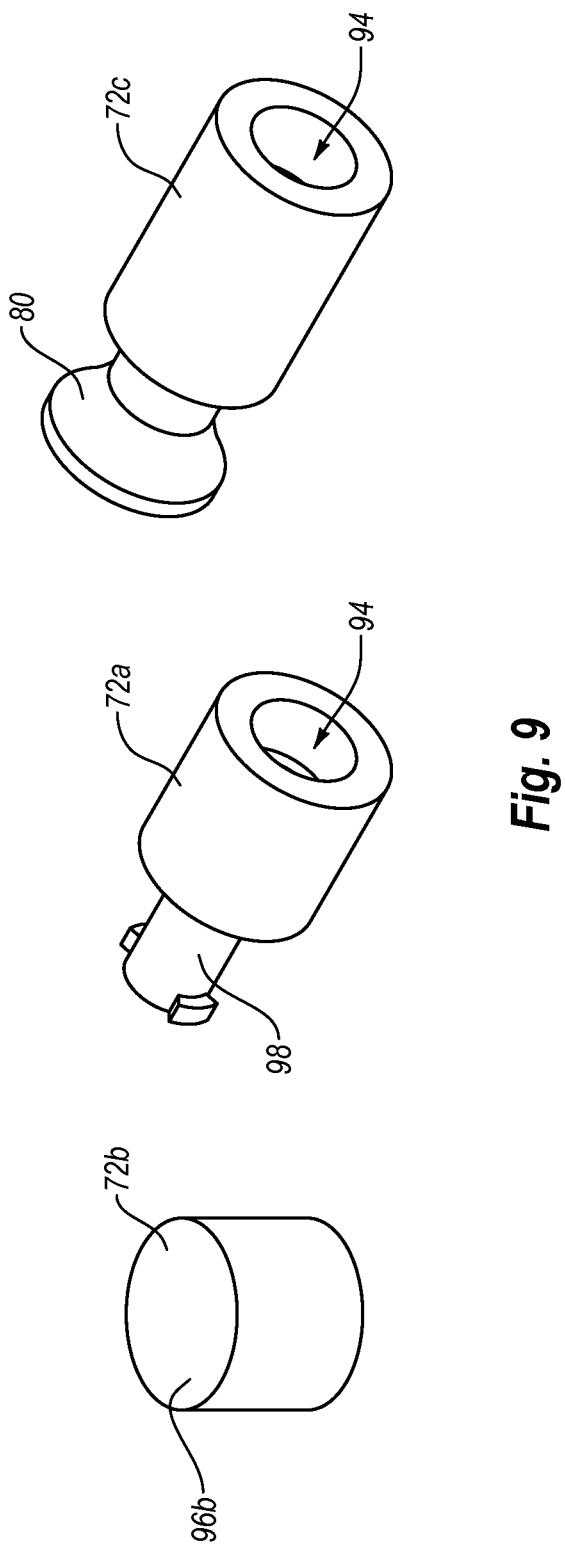

FIG. 9 shows the luer lock adapter 72a having the luer lock member 98, inactivity adapter cap 72b, and actuator adapter 72c having the actuator 80. These three adapters can be included with the feeding tube system 50 in a kit. These adapters can be extruded plastic or molded; and can be attached to the port 84 via thin strips to keep them all together. That is, flexible bands (not shown) can couple each of the adapters of FIGS. 8-9 together, and any of the adapters can be removably coupled to the port 84 of the feeding tube system 50. Also, the port 84 can be a single port, double port, or triple port, and the adapters can be provided for each of the separate port opening in the port 84. A switch mechanism can be included in the port 84 to determine which of the adapters is fluidly coupled with the feeding tube 52.

FIG. 10 illustrates an embodiment of the maneuverable feeding tube system 50. As shown, the feeding tube system 50 includes the feeding tube 52 coupled to a port 84, where the maneuverable tube 54 is located in the feeding tube 52. The port 84 is coupled to the adapter 72, and the maneuverable tube 54 (located in the lumen 62 of the feeding tube 52) having the control member 56 extends through the port 84. The control member 56 passes through the adapter 72 and is coupled with the actuator member 80. The actuator member 80 is shown to be shaped similar to a golf tee, which can be pulled to bend the distal end 58 or flexible portion 53 of the maneuverable tube 54 and released to relax and extend the distal end 58 or flexible portion 53 of the maneuverable tube 54. The actuator member 80 can be pushed to extend or straighten the distal end 58 or flexible portion of the maneuverable tube 54. The actuator member 80 and adaptor 72 can function as a handle for the control member 56, which can be a wire or cord. The actuator member 80 may also be configured as a joystick such that actuation thereof manipulates the control member 56 to bend the flexible portion 53 of the maneuverable tube 54.

Figure 11:
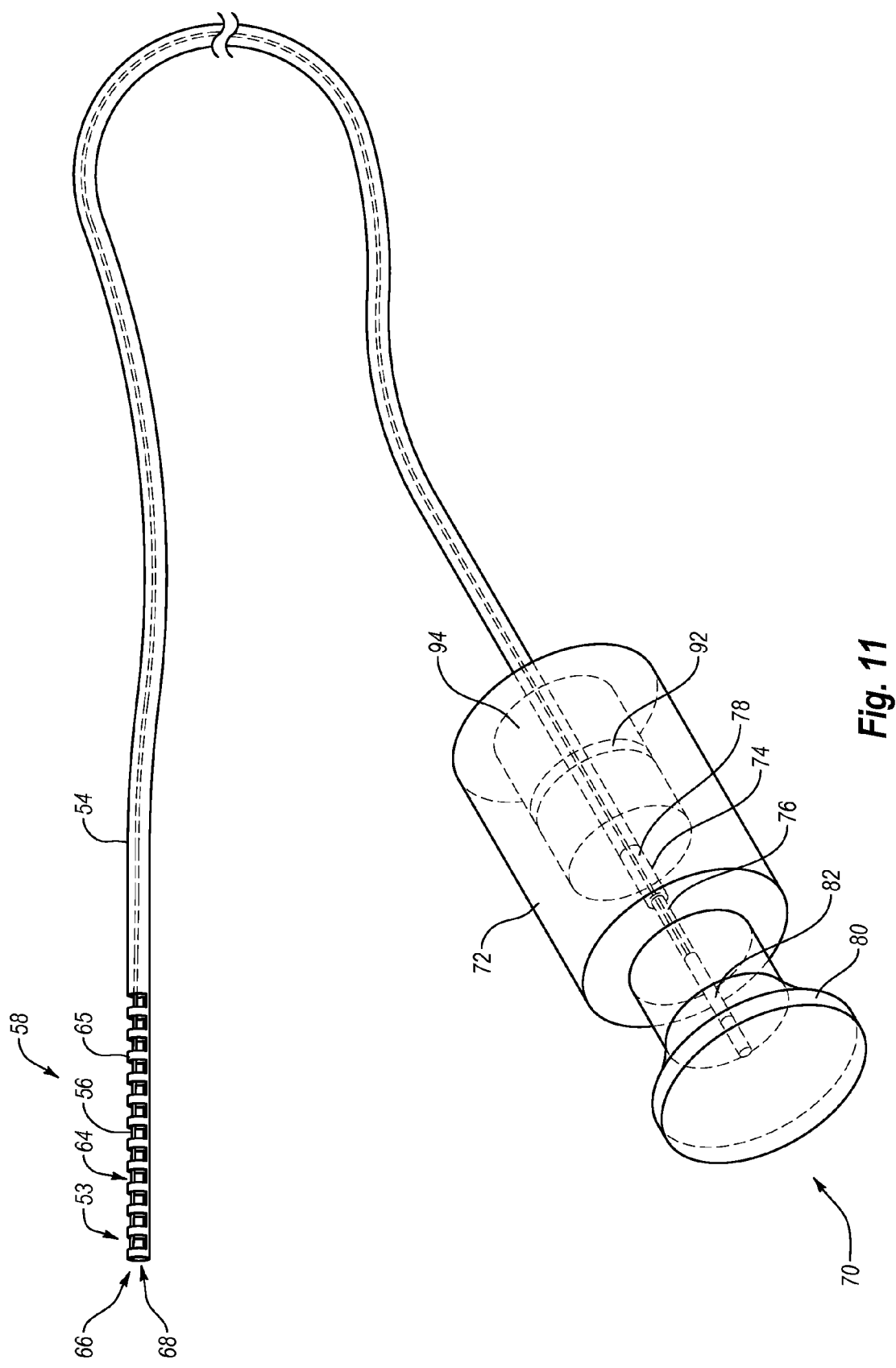
FIG. 11 illustrates an embodiment of a maneuverable tube of a feeding tube system.

FIG. 11 illustrates an embodiment of a maneuverable feeding tube guide system 50 having a maneuverable tube 54 that functions as a maneuverable feeding tube guide. While not shown, the feeding tube 52 can be included. Alternatively, the feeding tube can be slid over the maneuverable tube 54 once positioned. The actuator member and/or actuator adapter can be decoupled from the maneuverable tube, and the feeding tube can be slid over the maneuverable tube into position, such that the maneuverable tube functions as a guide wire. The control member 56 can also be used as a guide wire. The maneuverable tube 54 of the feeding tube system 50 is shown to include the distal end 58 having the flexible portion 53 with the flex gaps 64 and flex member 65. The lumen 66 is shown having the distal opening 68. The maneuverable tube 54 includes the proximal end 70 that is received through the adapter 72, and the control member 56 is operably coupled with the actuator member 80. The maneuverable tube 54 is shown to include the control member 56 strung along within the lumen 66 adjacent to the flex member 65 and exposed through the flex gaps 64. However, it is noted that the control member 56 appears to form an inner tube located within the lumen 66, but the control member 56 is merely just placed next to the lumen 66 inner wall. There is no tube within the maneuverable tube 54, unless the control member 56 is in a tube format. The proximal end 70 includes an adapter 72 that is configured to couple with a proximal end or port member of the feeding tube 52 as described herein. The adapter 72 includes a distal recess 74 configured to receive or couple with the feeding tube 52 by being dimensioned to receive the proximal end or port. The distal recess 74 is fluidly coupled with an internal conduit 76 that allows the maneuverable tube 54 and the control member 56 to extend therethrough. Also, the distal recess 74 can be coupled with the maneuverable tube 54 via a coupling member 78 such that only the control member 56 passes through the conduit 76. The control member 56 can extend through the conduit 76 so as to be coupled with an actuator member 80, which is illustrated as a shape similar to a golf tee; however, the actuator member 80 can have substantially any shape and may even have handle features. The actuator member 80 can include a recess 82 that receives the control member 56, which is coupled therewith. The actuator member 80 may also be referred to as a handle because it is handled in order to manipulate the control member 56, which when pulled bends the distal end 58 and flexible portion 53 of the maneuverable tube 54, and when pushed straightens the distal end 58 and flexible portion 53.

While not shown, the feeding tube system 50 can include radiopaque members or radiopaque indicia that can be viewed during fluoroscopy. The radiopaque members or indicia can be located anywhere on the feeding tube 52 and/or the maneuverable tube 54. The control member 56 may also be made from a radiopaque material or it may also have radiopaque members or indicia to facilitate viewing with fluoroscopy.

In one embodiment, the feeding tube system 50 can be devoid of radiopaque members or indicia. Such a configuration would not use fluoroscopy for placement, where the practitioner can use "feel" to place the feeding tube 52 into the small intestine. After some experience, "feel" of the device can be sufficient for accurate placement.

The present invention also includes methods of making the feeding tube system and methods of deploying the feeding tube using the feeding tube system.

In one embodiment, the present invention can be manufactured by standard techniques using standard or custom materials suitable for being passed into a human body. That is, the materials can be biocompatible and can have the proper flexibility or resilient flexibility. The materials can be resiliently flexible so that the tubes attempt to straighten after being bent during a maneuvering protocol. The tubes of the system can be premanufactured, and obtained in order to manufacture the feeding tube system.

Once the tube for the maneuverable tube is obtained, it can be cut in order to obtain the flex members and the flex gaps can be cutout from the tube. That is, the flex members can be formed by removing portions of the tube, where the removed portions form the flex gaps. However, prior to forming the flex members, the size and location of the flex members can be determined. The equations provided herein can be used to design the maneuverable portion of the maneuverable tube that has the flex members. The number and size of the flex members can be determined or calculated. The flex members can be cut into the maneuverable tube to a depth that is a fraction of the diameter of the maneuverable tube so that a portion of the maneuverable tube is retained as shown. The flex members can be cut out to be about 25%, about 33%, about 50%, about 66% to about 75% of the diameter of the maneuverable tube or of the circumference of the maneuverable tube. In any configuration, the tube of the maneuverable tube should be structurally sufficient to perform the functions described herein. The flex members can be cut with a sharp instrument or with a laser cutter. Alternatively, the maneuverable tube can be formed to already have the flex members, which can be by molding.

The control member, which can be a strip, tube, wire, or cord, can be coupled to the maneuverable tube before or after formation of the flex members; however, coupling the control member to the maneuverable tube after formation of the flex members may be preferred. The control member can be coupled to the maneuverable tube by various fastener mechanisms or adhesives. That is, a coupling can be used to couple the control member to the maneuverable tube, or an adhesive can be used to bond the control member to the maneuverable tube. The control member, when a wire or cord, can also be tied to the maneuverable tube, which can include the control member being tied to a body portion that defines one of the flex members. The maneuverable tube may also have a hole near the distal end that the control member can be tied to.

The port and adapter members can be prepared by machining, molding, or rapid prototyping, or solid member printing. The luer lock portion or actuator member can be formed by any manner and associated with the adapters. The actuator member may be coupled to the actuator adaptor by the control member extending through the actuator adaptor and being coupled to the actuator member.

The control member can be coupled with the actuator member such as by being received into a recess thereof, or tied thereto, or adhered thereto. A coupling member can be used to attach the control member with the actuator member. The maneuverable tube can also be received into and coupled with a lumen of the adapter.

Tygon PVC tubing can be used for the main feeding tube for its soft durometer (around 55 A) in order to be easily manipulated by the maneuverable tube. The maneuverable tube can be prepared from Teflon or polytetrafluoroethylene (with a durometer of 50 D, which is relatively hard). At the tip of the Teflon tube, rectangular notches the depth of two thirds the diameter of the Teflon tube can be cut to for the flex gaps and flex members. The flex gaps can be dimensioned, either depth-wise or longitudinally in order to allow for less resistance to bending by the control member. Kevlar string can be strung through the length of the maneuverable tube and coupled (e.g., tied) to the last flex member. The maneuverable tube having the notched tube section can be inserted into the Tygon PVC tubing. When the control member is pulled, the tip of the tube can be bent to or past 90°, or even to 180 degrees depending on the configuration of the flex gaps and flex members. FIGS. 6A-6C show the bendability. The diameter of the feeding tube can be below 0.160 inches, which can be a common diameter of feeding tubes.

In one embodiment, the material of the maneuverable tube can be selected in order to obtain a stiffer durometer of about 50 D. This longitudinal stiffness prevents the maneuverable tube from undergoing an accordion collapse affect when being pulled by the control member. This stiffness can also provide the maneuverable tube more structural integrity than the feeding tube to facilitate bending at the distal end. The maneuverable tube can be slightly stiffer than the feeding tube in order to ease the insertion process even more.

In one embodiment, both the feeding tube and maneuverable tube can be prepared from the same type of polymer, but with the maneuverable tube having a greater longitudinal and/or lateral stiffness. For example, both can be of different polyurethanes. With different formulations of polyurethanes, the relative hardness or stiffness can be adjusted.

In one embodiment, the control member can be prepared from any type of wire, and may be prepared of a common guide wire material used for catheters. Also, a monofilament similar to the fishing line can be used, and a multi-filament can be used.

In one embodiment, the system or kit can include all three adapters. The adapters can be separate, or they can be coupled together with a flexible member. The different adapters allows for a single hole in the port, which can be removably coupled to any of the different adapters. The actuator adaptor can be used during placement of the distal end of the feeding tube via the distal end of the maneuverable tube being maneuvered. The cap adaptor can be used to plug or seal the port. The luer lock adaptor can be used to couple the port to a feeding tube reservoir. Also, the luer lock adaptor can be modified to be different from a luer lock, but to have a similar rotatable fastener mechanism that attaches to a food reservoir with a compatible rotatable fastener mechanism.

In one embodiment, a single adaptor can have both the actuator adaptor portion and the luer lock portion. For example, the luer lock portion can be associated with the side of the actuator adaptor. This allows for the actuator adaptor to be used, and then the luer lock portion to be used. When combined, the actuator member and maneuverable tube as well as the control member can be withdrawn from the actuator adaptor, and the cap can be placed thereon to seal the adaptor. The luer lock portion can then be coupled to a food reservoir.

In one embodiment, the length of the feeding tube and/or maneuverable tube can be dependent on the target subject, which can range in size appropriate for a newborn, infant, child, adolescent, teen, or adult. For example, the length can vary between 36 and 55 inches, or longer for taller people, or shorter for teens, children, infants, babies, and premature babies.

A mathematical model can be used in order to determine a bending moment for the flexible portion based on the elastic modulus of the material. The moment of inertia and the curvature of the tip movement can be used to find the moment. The curvature of the tip can be determined by assuming a 1.5-inch section to be the flexible section, which can be configured to be bent to any angle. For one example, the final angle of bending can be about 45 degrees. Once the mathematical model is created, several tubes can be compared. Examples of the tubes can include McMaster Carr: 0.125 inch outer diameter clear Tygothane polyurethane tubing; 0.125 inch outer diameter antimicrobial blue polyethylene tubing; and 0.0625 inch outer diameter Extreme-Temp Teflon tubing.

The mathematical model can be used in designing the feeding tube system, and can be used to compare different materials and their bending characteristics in tube form. Bending stiffness is defined as:

$$M = EIk = EI\frac{d^2w}{dx^2} = EI\frac{1}{r}$$

Where E is the modulus of Elasticity of the material and I is the moment of inertia:

$$I = \frac{\pi}{64}(d_0^4 - d_i^4)$$

k is defined as the curvature of the bend. It can also be defined as the inverse of the radius of curvature:

$$k = \frac{1}{R}$$

This provides a way to define the amount of force needed to create a certain bend with a specified radius. We decided to assume some things about the curve.

Length of bent section=Circumference/8=1.5 inch
Angle of bend=45°

$$\frac{C}{8} = \frac{2\pi r}{8} = 1.5$$

From this, r=1.91 inches. The inverse of this, curvature k, was then equal to 0.524. From these calculations, material properties of different possible material choices can be compared.

In one embodiment, the present invention can include a model of the gastrointestinal tract. That is, the system or kit can include a model that can be used for distal end placement practice. A realistic model of the gastrointestinal tract can be created for practicing placement of the distal end of the feeding tube system described herein. The shape of the nose and esophagus can be prepared from a flexible tube, and a hole can be cut where the trachea anatomically exits the throat. Another tube can be used for the trachea, which tube is coupled to the hole representing the tracheal opening. The model tubing can be set in shape by any manner, such as by being attached to a pegboard to keep its shape. A container, such as with a 2 L volume, can be prepared into the shape of a stomach having a top opening and a bottom opening. One end of the stomach model can be attached to the flexible tubing to similar the esophagus attachment to the stomach. Optionally, another flexible tube can be attached to the bottom of the stomach model to simulate the intestine. The placement of the distal end of the feeding tube system past the stomach model or into the simulated intestine can be practiced with the model.

Once the feeding tube and maneuverable tube with control member have been obtained, the maneuverable tube can be placed within the lumen of the feeding tube. The relative position of the tubes can be similar such that the openings thereof are adjacent. The bendable portion of the maneuverable tube can be located near the distal tip of the feeding tube to obtain suitable bendability. The feeding tube and maneuverable tube with control member can be provided together or separately and then combined. The distal end of the maneuverable tube can be inserted into the proximal end of the feeding tube and relatively slid to obtain the distal ends of both tubes being aligned or otherwise positioned as described herein. The proximal end of the feeding tube can include the port before the maneuverable tube is inserted through the proximal end. The port can then be fastened to the adapter. The maneuverable tube or control Member can be coupled to the adapter and actuator member, respectively, after the maneuverable tube is inserted into the feeding tube having the port.

The maneuverable feeding tube system described herein can be deployed using traditional methods of delivering feeding tubes, except that the bendable portion of the system (e.g., having the flexible portion of the maneuverable tube in the feeding tube) allows for the distal end of the system to be bent during the placement procedure. That is, the practitioner placing the feeding tube system can bend the distal end of the maneuverable tube as needed or desired. The bending can be used to facilitate passing through the stomach or pyloric sphincter (pylorus). The placement can be conducted with or without using fluoroscopy. When fluoroscopy is used, a practitioner can use an image of the system on a screen in order to determine when and how much to bend the bendable portion.

During placement, the practitioner can use the peristaltic movement of the stomach to pass therethrough. Also, the practitioner can push the distal end through the stomach and pylorus. The placement can be done to avoid the feeding tube bending or coiling in the stomach or perforating the stomach. When needed, the practitioner can actuate the actuator member so as to pull the control member to bend the maneuverable tube at the distal end. This can allow for the practitioner to be capable of accurately placing the feeding tube. Pushing the actuator member can push the control member and straighten the distal end. Also, relaxing the control member may also straighten the distal end. The flexible distal end can be selectively bent and straightened at any time during placement, such as when passing the tracheal opening, past the lower esophageal sphincter, through the stomach or pylorus.

Once the feeding tube is in place, the practitioner can uncouple the adapter from the port, and the maneuverable tube can be extracted from the feeding tube. The extraction can be by pulling the control member and/or the maneuverable tube. The adapter can be configured such that it can be grasped in order to facilitate extraction. Also, the adapter that is uncoupled can be the actuator adaptor, and the cap adaptor or luer lock adapter can be mounted to the port as desired or needed.

Once the maneuverable tube has been extracted, the feeding tube can be used to administer food and nutrition to the small intestine. As such, the port can be coupled to a nutritional reservoir that includes a nutritional medium. For example, the luer lock adaptor can be coupled to a nutritional reservoir.

In one instance, it may be desirable to replace the feeding tube with a new feeding tube. As such, a guide wire can be passed through the lumen of the feeding tube to the placement location of the distal opening. The feeding tube can then be extracted over the guide wire, and a new feeding tube can be deployed to the small intestine by being passed over the guide wire. This is similar to the Seldinger Technique mentioned before used with catheters. The maneuverable tube can be used as the guide wire or as a guide tube in this manner, such that the old feeding tube can be extracted over the maneuverable tube and a new feeding tube can be slid over the maneuverable tube and into the proper placement. The maneuverable tube can then be extracted through the new feeding tube.

In one instance a maneuverable feeding tube system can be passed over the guide wire, and once the distal end passes over the distal end of the guide wire the maneuverable tube can be maneuvered for placement of the distal opening at another location within the small intestine.

While the present invention has been generally described above, the following disclosure provides additional details of the present invention.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g.; "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

Tables

TABLE 1

Possible material choices based on outcomes of the mathematical model.

| Type of Material | $D_o$ (in) | $D_i$ (in) | Area Moment of Inertia (in$^4$) | Modulus of Elasticity (psi) | Designated Product Bend Radius (in) | Bend Radius (in) | Curvature (1/in) | Moment (in-lb) |
|---|---|---|---|---|---|---|---|---|
| Polyurethane | 0.12 | 0.06 | 1.123E−05 | 800 | 0.1875 | 1.91 | 0.5235602 | 0.0047058 |
| Polyethylene | 0.12 | 0.06 | 1.123E−05 | 125,000 | 0.3125 | 1.91 | 0.5235602 | 0.7352886 |
| Teflon ® PTFE (Polytetrafluoroethylene) | 0.06 | 0.03 | 7.022E−07 | 80,000 | 0.125 | 1.91 | 0.5235602 | 0.0294115 |

TABLE 1-continued

Possible material choices based on outcomes of the mathematical model.

| Type of Material | $D_o$ (in) | $D_i$ (in) | Area Moment of Inertia (in⁴) | Modulus of Elasticity (psi) | Designated Product Bend Radius (in) | Bend Radius (in) | Curvature (1/in) | Moment (in-lb) |
|---|---|---|---|---|---|---|---|---|
| Vinyl (lower bound) | 2.3 | 1.67 | 0.9918664 | 230 | — | 1.91 | 0.5235602 | 119.43941 |
| Vinyl (upper bound) | 2.3 | 1.67 | 0.9918664 | 470 | — | 1.91 | 0.5235602 | 244.07184 |

The invention claimed is:

1. A maneuverable feeding tube system comprising:
a feeding tube device comprising:
   a feeding tube having an internal lumen extending from a proximal end having a proximal opening to a distal end having a distal opening; and
   a port coupled to the proximal end of the feeding tube, the port having a port lumen extending from a first port end to a second port end, the port lumen being a segmented lumen and having a first lumen opening at the first port end and a second lumen opening at the second port end, the first lumen opening being larger than the second lumen opening, the segmented lumen having a first lumen segment having the proximal end of the feeding tube located therein such that the feeding tube extends from the first lumen opening, the segmented lumen having a second lumen segment extending from the first segment to the second lumen opening, wherein the first lumen segment has a larger cross-sectional dimension than the second lumen segment, the port having an adapter-receiving surface with a first fastener member; and
a maneuverable tube device that is slideably removable from the internal lumen of the feeding tube, the maneuverable tube device comprising:
   a maneuverable tube dimensioned to be located within the internal lumen of the feeding tube, the maneuverable tube having a proximal end and a flexible distal end that when located within the internal lumen of the feeding tube the flexible distal end is associated with the distal opening of the feeding tube, wherein the flexible distal end includes one or more flex members;
   an elongate control member having a first end coupled to the flexible distal end of the maneuverable tube and the elongate control member extending through the maneuverable tube and from the proximal end; and
   an actuator adapter coupled to the proximal end of the maneuverable tube and having an actuator member coupled to a second end of the elongate control member, the actuator adapter having a port-receiving surface that is configured to be removably coupled to the adapter-receiving surface of the port such that the control member extends from the actuator member through an internal conduit of the actuator adapter, the port-receiving surface having a second fastener member configured to couple with the first fastener member.

2. The maneuverable feeding tube system of claim 1, the at least one adapter comprising one or more of:
a ported adapter having a ported end, the ported adaptor having a port-receiving surface that is configured to be removably coupled to the adapter-receiving surface of the port such that the ported adapter is fluidly coupled with the feeding tube, the port-receiving surface having a second fastener member configured to couple with the first fastener member; or
an adapter cap having a port-receiving surface that is configured to be removably coupled to the adapter-receiving surface of the port, the adapter cap sealing the port when coupled thereto, the port-receiving surface having a second fastener member configured to couple with the first fastener member.

3. The maneuverable feeding tube system of claim 2, comprising the actuator adapter, ported adapter, and adapter cap being flexibly coupled together through elongate flexible strap members.

4. The maneuverable feeding tube system of claim 1, wherein:
the feeding tube includes a durometer of about 55 A or more flexible; or the maneuverable tube includes a durometer of about 55A or stiffer.

5. The maneuverable feeding tube system of claim 1, wherein the one or more flex members at least partially define flex gaps located between two adjacent flex members.

6. The maneuverable feeding tube system of claim 1, wherein the one or more flex members are located on one side of the maneuverable tube.

7. The maneuverable feeding tube system of claim 1, comprising two or more control members, each coupled to the maneuverable tube at the flexible distal end on opposite sides.

8. The maneuverable feeding tube system of claim 1, wherein one or more of the feeding tube, maneuverable tube, and control member include one or more radiopaque members or radiopaque indicia.

9. The maneuverable feeding tube system of claim 1, wherein one or more of the feeding tube, maneuverable tube, or control member is devoid of a radiopaque material.

10. The maneuverable feeding tube system of claim 1, wherein the port has a single lumen which is the segmented lumen, the single lumen extending from the first port end to the second port end.

11. The maneuverable feeding tube system of claim 1, wherein the port has a segmented external shape, the segmented external shape having a tapered distal portion and a cylindrical proximal portion.

12. The maneuverable feeding tube system of claim 1, wherein the first fastener member and second fastener member are cooperatively configured to fasten to each other and selected from snap members, threaded members, friction fittings, or male-female members.

13. The maneuverable feeding tube system of claim 12, wherein the first fastener member and second fastener member are snap members with one having an annular protrusion that fits into an annular recess of the other.

14. The maneuverable feeding tube system of claim 13, wherein the first fastener member includes the annular protrusion and the second fastener member includes the annular recess.

15. The maneuverable feeding tube system of claim 2, comprising:
   the ported adapter; and
   the adapter cap.

16. The maneuverable feeding tube system of claim 15, further comprising the actuator adapter, ported adapter, and adapter cap each being flexibly coupled to the port through elongate flexible strap members.

17. The maneuverable feeding tube system of claim 1, wherein the adapter-receiving surface is on an external surface of the port, and the port-receiving surface is located on an internal recess or lumen of the actuator adapter.

18. A method of manufacturing the maneuverable feeding tube of claim 1, the method comprising:
   obtaining the feeding tube;
   obtaining a smaller tube having a cross-sectional profile that fits within the internal lumen of the feeding tube;
   forming flex members into the smaller tube at the distal portion thereof to form the maneuverable tube;
   coupling the control member to the flexible distal portion of the maneuverable tube; and
   combining the maneuverable tube with the feeding tube such that the maneuverable tube is located within the feeding tube such that their distal openings are associated.

19. A method of placing a feeding tube in a small intestine, the method comprising:
   providing the maneuverable feeding tube system of claim 1;
   inserting a distal end of the maneuverable feeding tube system into a nostril of a subject;
   pushing the distal end of the maneuverable feeding tube system to the stomach with or without bending the flexible distal end of the maneuverable tube;
   pushing the distal end of the maneuverable tube past the pylorus with or without bending the flexible distal end of the maneuverable tube; and
   locating the distal opening of the feeding tube within the small intestine.

20. The method of claim 19, further comprising one or more of:
   selectively bending the flexible distal end of the maneuverable tube by pulling the control member by actuating an actuation member coupled to the control member;
   disengaging an actuator adapter from the port;
   withdrawing the maneuverable tube from the feeding tube;
   coupling an adapter cap to the port;
   coupling a ported adapter to the port; or
   coupling a medical device of food reservoir to the ported adapter.

21. The method of claim 19, comprising:
   introducing a guide wire into the internal lumen of the feeding tube;
   pushing the guide wire to the distal opening of the feeding tube;
   withdrawing the feeding tube over the guide wire;
   placing a new feeding tube over the guide wire; and
   locating the distal opening of the new feeding tube to a distal end of the guide wire so as to be in the small intestine.

* * * * *